United States Patent
Darley (10) Patent No.: US 7,519,434 B2
(45) Date of Patent: Apr. 14, 2009

(54) ELECTRODE ARRAY FOR A COCHLEAR IMPLANT HAVING ONE OR MORE ADJUSTABLE ELECTRODES

(75) Inventor: Derek I. Darley, Cromer Heights (AU)

(73) Assignee: Cochlear Limited, Lane Cove, NSW (AU)

( * ) Notice: Subject to any disclaimer, the term of this patent is extended or adjusted under 35 U.S.C. 154(b) by 0 days.

(21) Appl. No.: 10/512,201

(22) PCT Filed: Apr. 17, 2003

(86) PCT No.: PCT/AU03/00463

§ 371 (c)(1),
(2), (4) Date: Sep. 19, 2005

(87) PCT Pub. No.: WO03/090848

PCT Pub. Date: Nov. 6, 2003

(65) Prior Publication Data

US 2006/0089700 A1    Apr. 27, 2006

(30) Foreign Application Priority Data

Apr. 23, 2002   (AU) .................................... PS1923

(51) Int. Cl.
*A61N 1/00*   (2006.01)

(52) U.S. Cl. .................................................. 607/137

(58) Field of Classification Search ......... 600/372–381; 607/98, 116–137; 362/171; 333/204; 310/251
See application file for complete search history.

(56) References Cited

U.S. PATENT DOCUMENTS

| | | | | |
|---|---|---|---|---|
| 4,284,085 | A * | 8/1981 | Hansen et al. | 607/137 |
| 4,358,699 | A * | 11/1982 | Wilsdorf | 310/251 |
| 4,573,481 | A | 3/1986 | Bullara | |
| 5,037,497 | A * | 8/1991 | Stypulkowski | 156/245 |
| 5,645,585 | A * | 7/1997 | Kuzma | 623/10 |
| 5,825,264 | A * | 10/1998 | Yamazaki et al. | 333/204 |
| 6,119,044 | A | 9/2000 | Kuzma | |
| 6,520,660 | B1 * | 2/2003 | Ho | 362/171 |
| 2004/0110123 | A1 * | 6/2004 | Maher et al. | 435/4 |

* cited by examiner

*Primary Examiner*—George Manuel
(74) *Attorney, Agent, or Firm*—Connolly Bove Lodge & Hutz LLP (57) ABSTRACT

An electrode array for a tissue-stimulating prosthesis, such as a cochlear implant. The electrode array is comprised of a plurality of electrodes (41), wherein at least one electrode of the array is comprised of at least two electrically connected portions (41a, 41b) that are adjustable in orientation relative to each other. This adjustability in orientation preferably allows the array to adopt a tighter curvature than would be the case were the electrode portions not relatively adjustable to each other.

31 Claims, 5 Drawing Sheets

ELECTRODE ARRAY FOR A COCHLEAR IMPLANT HAVING ONE OR MORE ADJUSTABLE ELECTRODES

FIELD OF THE INVENTION

The present invention relates to an implantable electrode array and, in particular, a cochlear implant electrode assembly.

BACKGROUND OF THE INVENTION

Hearing loss, which may be due to many different causes, is generally of two types, conductive and sensor neural. In some cases, a person may have hearing loss of both types. Of them, conductive hearing loss occurs where the normal mechanical pathways for sound to reach the hair cells in the cochlea are impeded, for example, by damage to the icicles. Conductive hearing loss may often be helped by use of conventional hearing aids, which amplify sound so that acoustic information does reach the cochlea and the hair cells.

In many people who are profoundly deaf, however, the reason for their deafness is sensor neural hearing loss. This type of hearing loss is due to the absence of, or destruction of, the hair cells in the cochlea which transduce acoustic signals into nerve impulses. These people are thus unable to derive suitable benefit from conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibres, thereby allowing the brain to perceive a hearing sensation resembling the natural hearing sensation normally delivered to the auditory nerve.

Cochlear implant systems have generally consisted of essentially two components, an external component commonly referred to as a processor unit and an internal implanted component commonly referred to as a receiver/stimulator unit. Traditionally, both of these components have cooperated together to provide the sound sensation to a recipient.

The external component has traditionally consisted of a microphone for detecting sounds, such as speech and environmental sounds, a speech processor that converts speech into a coded signal, a power source such as a battery, and an external transmitter coil.

The coded signal output by the sound processor is transmitted transcutaneously to the implanted receiver/stimulator unit situated within a recess of the temporal bone of the recipient. This transcutaneous transmission occurs via the external transmitter coil which is positioned to communicate with an implanted receiver coil provided with the receiver/stimulator unit. This communication serves two essential purposes, firstly to transcutaneously transmit the coded sound signal and secondly to provide power to the implanted receiver/stimulator unit. Conventionally, this link has been in the form of a radio frequency (RF) link, but other such links have been proposed and implemented with varying degrees of success.

The implanted receiver/stimulator unit traditionally includes a receiver coil that receives the coded signal and power from the external processor component, and a stimulator that processes the coded signal and outputs a stimulation signal to an intracochlea electrode assembly which applies the electrical stimulation directly to the auditory nerve producing a hearing sensation corresponding to the original detected sound.

It is known in the art that the cochlea is tonotopically mapped. In other words, the cochlea can be partitioned into regions, with each region being responsive to signals in a particular frequency range. This property of the cochlea has been exploited by providing the electrode assembly with an array of electrodes, each electrode being arranged and constructed to deliver a stimulating signal within a preselected frequency range, to the appropriate region within the scala tympani of the cochlea. The electrical currents and electric fields from each electrode stimulate the nerves disposed on the modiolus of the cochlea.

To achieve good positioning of the electrode assembly, it is desirable that the array be inserted relatively deeply into the scala tympani of the cochlea and positioned as close as possible to the inner wall of the cochlea to enable direct stimulation of the appropriate auditory nerves cells disposed in the modiolus of the cochlea. For this reason, electrode arrays having a shape adapted to conform to the shape of the modiolus of the cochlea have been developed, such as that described in the Applicant's U.S. Pat. No. 6,421,569.

The present invention therefore assists in achieving this outcome to achieve optimal placement of the electrodes of the electrode array.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present application is directed to a first invention comprising an electrode array for a tissue-stimulating prosthesis, the electrode array comprising a plurality of electrodes, wherein at least one electrode of the array is comprised of at least two electrically connected portions that are adjustable in orientation relative to each other.

This adjustability in orientation preferably allows the array to adopt a tighter curvature than would be the case were the electrode portions not relatively adjustable to each other.

In one embodiment, the electrode array can comprise one of a plurality of stacked but laterally off-set electrode sets used for a tissue-stimulating prosthesis.

In a further embodiment, the array is supported in a carrier member. The carrier member can have a leading end and a trailing end. The array preferably extends from a position at or adjacent the leading end back along the carrier member towards the trailing end. In one embodiment, said at least one adjustable electrode is adjacent the leading end of the carrier member. In another embodiment, said at least one adjustable electrode can be at a location where adjustability is more likely to be required following insertion of the array. In one embodiment, the array can comprise adjustable electrodes interspersed between other non-adjustable electrodes. In one embodiment, at least some adjustable electrodes can be positioned side-by-side in the array.

Each adjustable electrode can comprise two or more portions. Each portion preferably extends outwardly from a common conducting portion. In one embodiment, a gap can be present between the portions of the electrode. In another embodiment, the gap can be bridged by one or more bridge members. In one embodiment, the bridge member can extend between the portions at a location distal the common conducting portion. Each or some of the bridge members can have a thickness equal to or different than that of the electrode portions. In another embodiment, the portions can be linked by a region that fully or substantially closes the gap and which has a thickness less than that of the adjacent portions. In one embodiment, the region that fully or substantially closes the gap can have a substantially V-shaped cross-section, with the electrode preferentially bendable at this location.

Each portion is preferably fabricated so as to be in a common plane and are then adjustable in orientation relative to this plane on implantation of the array. Each portion of each said adjustable electrode is preferably rectangular in shape, however any shape is envisaged as being within the scope of the present invention. Respective portions of each said adjustable electrode are also preferably of about equal dimensions. It will be appreciated that the respective portions could, however, be of different shapes and/or sizes compared to each other.

The respective portions of each said adjustable electrode are preferably separated by a gap. The gap is preferably present on manufacture of the electrode array. During implantation, the gap can be closed as the portions move towards one another. For example, if the carrier member adopts a spirally curved configuration, the respective portions can undergo a change in orientation relative to the said common plane and so come into contact with each other.

In a further embodiment, the electrodes are formed from a biocompatible conductive material such as platinum or iridium. The electrodes can be formed from a sheet of platinum or an alloy. The sheet or foil can have a thickness of between about 1, 2, 5 or 10 and 50 microns. Each formed electrode can have a conducting portion extending away there from to a location distal the electrode. Each portion of each of said adjustable electrodes has at least one common conducting portion extending away there from. Each conducting portion can extend lineally away from its electrode. The respective linear conducting portions are preferably aligned in a parallel arrangement. The conducting portions are hereinafter referred to as "wires" as they serve to provide electrical conduction between each electrode to a location distal the electrode array.

In a further embodiment, the electrodes and wires can be formed using machining processes as defined in International Patent Publication No WO 02/089907 of the present applicant. For example, the electrodes and wires can be formed using electrical discharge machining (EDM), milling, cutting, or etching.

In another embodiment, the electrodes and wires can be formed using conventional processes, such as those described in the Applicant's U.S. Pat. No. 6,421,569, the contents of which is incorporated herein by reference. In this regard, each of the electrodes can be a conductive pad, made from a suitable biocompatible material, such as platinum, with conventional wires welded to each of the electrodes providing electrical conduction between each electrode to a location distal the electrode array. Each portion of each of the adjustable electrodes has at least one conducting portion extending away there from.

In a preferred embodiment, the array comprises 30 electrodes, with the array comprising at least 4 of said adjustable electrodes. Where the array comprises 30 electrodes, the array can comprise 5 different sets of electrodes that have been formed individually and then stacked one on top of the other to form a single electrode array. Where the array comprises 30 electrodes, the array can comprise 3 sets of seven electrodes, 1 set of 5 electrodes and 1 set of 4 adjustable electrodes. In this embodiment, the 3 sets of 7 electrodes are stacked one on top of the other, the set of 5 electrodes is stacked on these sets, with the set of 4 electrodes on top of the stack. Other combinations of sets can, however, be envisaged, for example 1 set of 3 electrodes with adjustable electrodes at the tip to curve to a smaller radius, 1 set of 4, 1 set of 5 & 3 sets of 6.

While the sets of electrodes are stacked one upon the other, it will be appreciated that the actual position of the electrodes in each set are not necessarily vertically aligned. Rather, the set immediately above its lower set may be laterally offset so as to ensure the electrodes are visible from beneath the stack.

The wires extending from each electrode are preferably of the same length. It can, however, be envisaged that the wires could be formed with different lengths to account for the ultimate offset present when forming the stack.

Once the stack is formed, the hitherto at least substantially planar electrodes are preferably deformed so as to at least partially extend through a third dimension. In a preferred embodiment, each of the electrodes is curved out of the plane of the wires for each set of electrodes. The curvature can be substantially semi-circular. A mandrel can be used to form the curvature in the electrodes.

Once the electrodes have been deformed to have a substantially semi-circular curvature, each of the electrodes can be further folded about a longitudinal axis of the array. This folding of the electrodes preferably serves to bend the electrodes around the wires of the array. The electrodes can be folded individually, in small groups, or all together. In one embodiment, the electrodes are folded so as to define a lumen that extends through the array.

Once the electrode array is complete it can be encapsulated in a further layer of a biocompatible relatively insulating material to form the electrode carrier member. In a preferred embodiment, the biocompatible material can be a silicone, such as a flexible silicone elastomer-Silastic. Silastic MDX 4-4210 is an example of one suitable silicone for use in the formation of the carrier member. In another embodiment, the elongate carrier member can be formed from a polyurethane or similar material.

In another method, the body of the array can be formed, with the wiring then adhered to the array before the electrodes are bent around the body.

In one embodiment, the carrier member can be formed in a mould with the biocompatible material allowed to set around the array. In this embodiment, the electrodes are preferably positioned in the mould so as to not be coated with the biocompatible material. In one embodiment, the carrier member can be moulded in a straight configuration. In another embodiment, the carrier member can be moulded in a curved configuration, such as a spirally-curved configuration.

In a preferred embodiment, the electrode array is for use as an implantable tissue-stimulating device. More preferably, the tissue-stimulating device is a cochlear electrode assembly, more preferably an intracochlear electrode assembly.

In a preferred embodiment, the intracochlear electrode assembly is a part of an implanted component of a cochlear implant system. The implanted component further preferably comprises a receiver coil and a housing for a stimulator device. The carrier member preferably extends outwardly from the housing of the stimulator device.

In a further embodiment, the leading end of the carrier member is insertable into a cochlea of a recipient. The wires of the electrode array preferably extend back towards the trailing end of the carrier member.

The wires preferably extend back to the housing to at least a first feedthrough in the wall of the housing. The wires are preferably exposed at or adjacent the trailing end to allow connection to the feedthroughs. In one embodiment, the feedthrough provides hermetic and insulated electrical connection for each wire extending from the electrode assembly into the housing of the implantable component. Each feedthrough can be formed using the method described in U.S. Pat. No. 5,046,242, the contents of which are incorporated herein by reference.

In a preferred embodiment, the orientation of the carrier member as it is firstly inserted through a cochleostomy into the cochlea is preferably substantially straight. More preferably, the implantable orientation is straight. Following completion of implantation, the carrier member preferably adopts a spirally curved configuration that at least substantially matches the spiral nature of the scala tympani of the human cochlea. The carrier member is preferably pre-formed with this spiral configuration and is then straightened either during manufacture and packaging of the device or prior to implantation. The carrier member is preferably held straight prior to and at least during the initial stages of implantation by a stylet. The stylet preferably extends through a lumen of the carrier member such as the lumen described herein that is formed by the folding of the electrodes about the wires.

As the carrier member is inserted into the scala tympani of the cochlea, the degree of curvature required of the array becomes tighter if the array is to be implanted to a desired depth within the cochlea. The ability of the portions of the leading end electrodes to adjust in orientation relative to each other during this process serves to allow the carrier to adopt a tighter degree of curvature than would otherwise be the case.

Further, the provision of electrode elements having portions that are capable of adjusting in orientation relative to each other allows conventional electrode arrays to become more flexible along their length. This improved flexibility is achievable without needing to revert to smaller electrode elements of reduced surface area, which may reduce the ability of the electrode elements to provide optimum stimulation and broad current spread. Therefore, the present invention potentially opens up a new realm for electrode array design where flexibility and stiffness of the array can be reduced without the need for reducing the stimulating surface area of the array.

In a further embodiment, the housing is preferably implantable in a recess of the temporal bone adjacent the ear of the recipient that is receiving the output of the implant system. The housing is preferably formed from a biocompatible material or has a biocompatible coating. The housing can be coated with a layer of silicone or parylene.

As already discussed, the implantable component preferably also comprises a receiver coil. The receiver coil preferably comprises a wire antenna coil. The antenna coil can be comprised of at least one, and preferably at least two, turns of electrically insulated platinum or gold wire tuned to parallel resonance by a capacitor internal to the housing. The electrical insulation of the antenna coil can be provided by a flexible silicone moulding and/or silicone or polyurethane tubing. The external coil can be constructed in a similar fashion to the implanted coil or have a different construction.

The antenna coil is preferably external of the housing. Electrical connection between the antenna coil and componentry of the implantable componentry within the housing can be provided by two hermetic and electrically insulated ceramic feedthroughs or an electrical conductor. The ceramic feedthroughs can be formed using the method described in abovementioned U.S. Pat. No. 5,046,242.

The antenna coil of the implantable component preferably acts as part of the radio frequency (RF) link to allow transcutaneous bidirectional data transfer between the implantable component and external components of the cochlear implant system. The radio frequency signals can comprise frequency modulated (FM) signals. While described as a receiver coil, the receiver coil can preferably transmit signals to the transmitter coil which receives the signals.

The link between the two coils also provides a means of powering the componentry of the internal component. Where the implantable component further has an on-board or implantable power source, such as a rechargeable battery, the link can provide a means of inductively charging the battery when required.

The implanted housing preferably contains, in addition to the stimulator device, a receiver device. The receiver device is preferably adapted to receive signals from the external component.

The housing of the external component preferably houses a speech processor adapted to receive signals output by a microphone. In a preferred embodiment, the microphone can be mounted to the housing or an ear hook member. Other suitable locations for the microphone and/or the housing for the speech processor can be envisaged, such as a lapel of the recipient's clothing.

The speech processor encodes the sound detected by the microphone into a sequence of electrical stimuli following given algorithms, such as algorithms already developed for cochlear implant systems. The encoded sequence is transferred to the implanted receiver/stimulator device using the transmitter and receiver coils. The implanted receiver/stimulator device demodulates the FM signals and allocates the electrical pulses to the appropriate attached electrode by an algorithm which is consistent with the chosen speech coding strategy.

The external component preferably further comprises a power supply. The power supply can comprise one or more rechargeable batteries. The transmitter and receiver coils are used to provide power via transcutaneous induction to the implanted stimulator/receiver device and the electrode array.

While the implant system can rely on external componentry, in another embodiment, the microphone, speech processor and power supply can also be implantable. In this embodiment, these components can be contained within a hermetically sealed housing or the housing used for the stimulator device.

BRIEF DESCRIPTION OF THE DRAWINGS

By way of example only, a preferred embodiment of the invention is now described with reference to the accompanying drawings, in which.

PREFERRED MODE OF CARRYING OUT THE INVENTION

Figure 1:
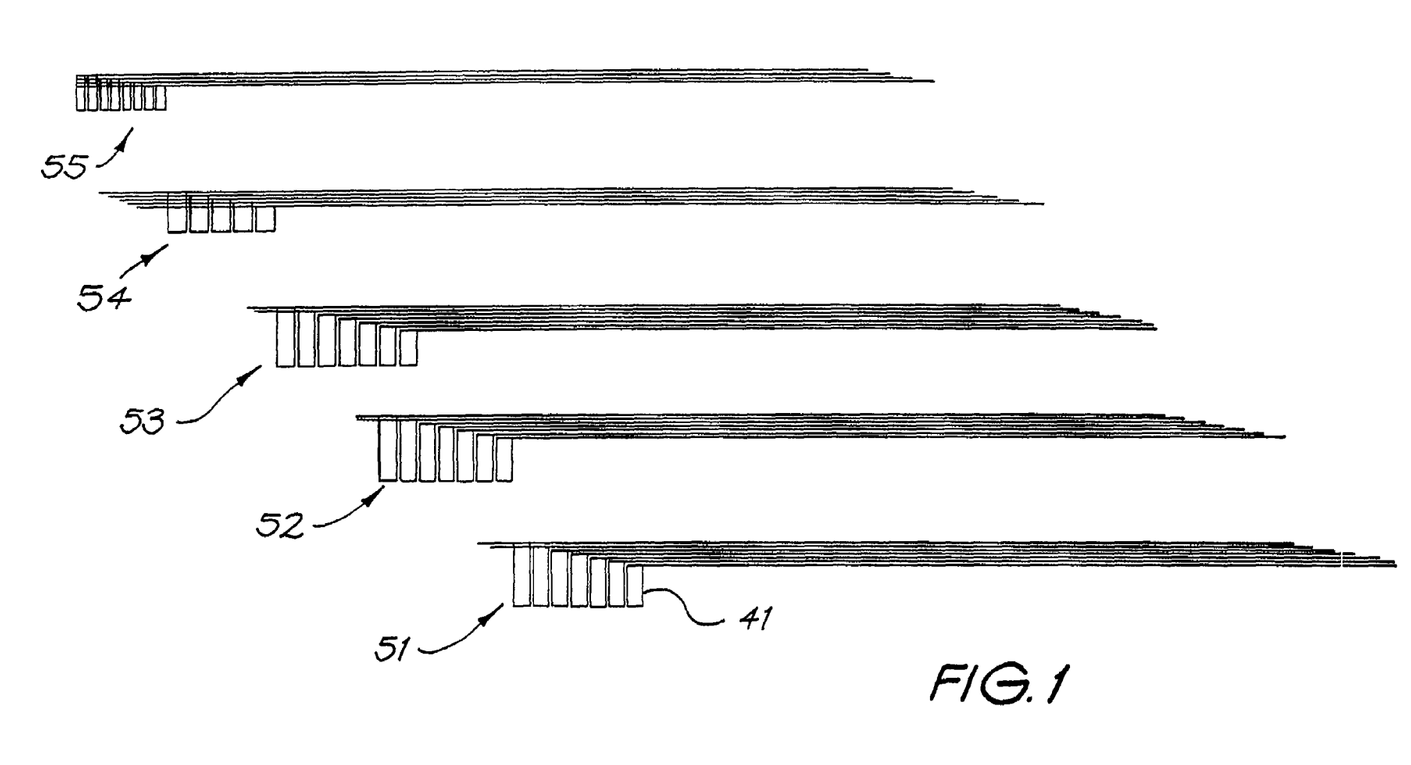
FIG. 1 is a plan view of a platinum sheet depicting how different sets of electrodes and adjoining wires can be formed in a platinum sheet through appropriate machining.

FIG. 1 depicts 5 different sets of electrodes and associated wires that have been formed on a single sheet of platinum foil. This figure depicts the electrode sets prior to them being trimmed from the platinum sheet. Each of the sets 51-55 have been formed in the sheet using electrical discharge machining (EDM) as defined in International Patent Publication No WO 02/089907 described above.

Once each of the sets 51-55 are formed, each set can be trimmed from the platinum sheet and stacked one above the other to form an aligned array of electrodes 41. In the embodiment depicted in FIG. 1, the electrode array comprises 30 electrodes, with the array comprising 3 stacked sets of 7 electrodes (51-53), 1 set of 5 electrodes (54) above these, and 1 set of 4 electrodes (55) on top of the stack.

Figure 2:
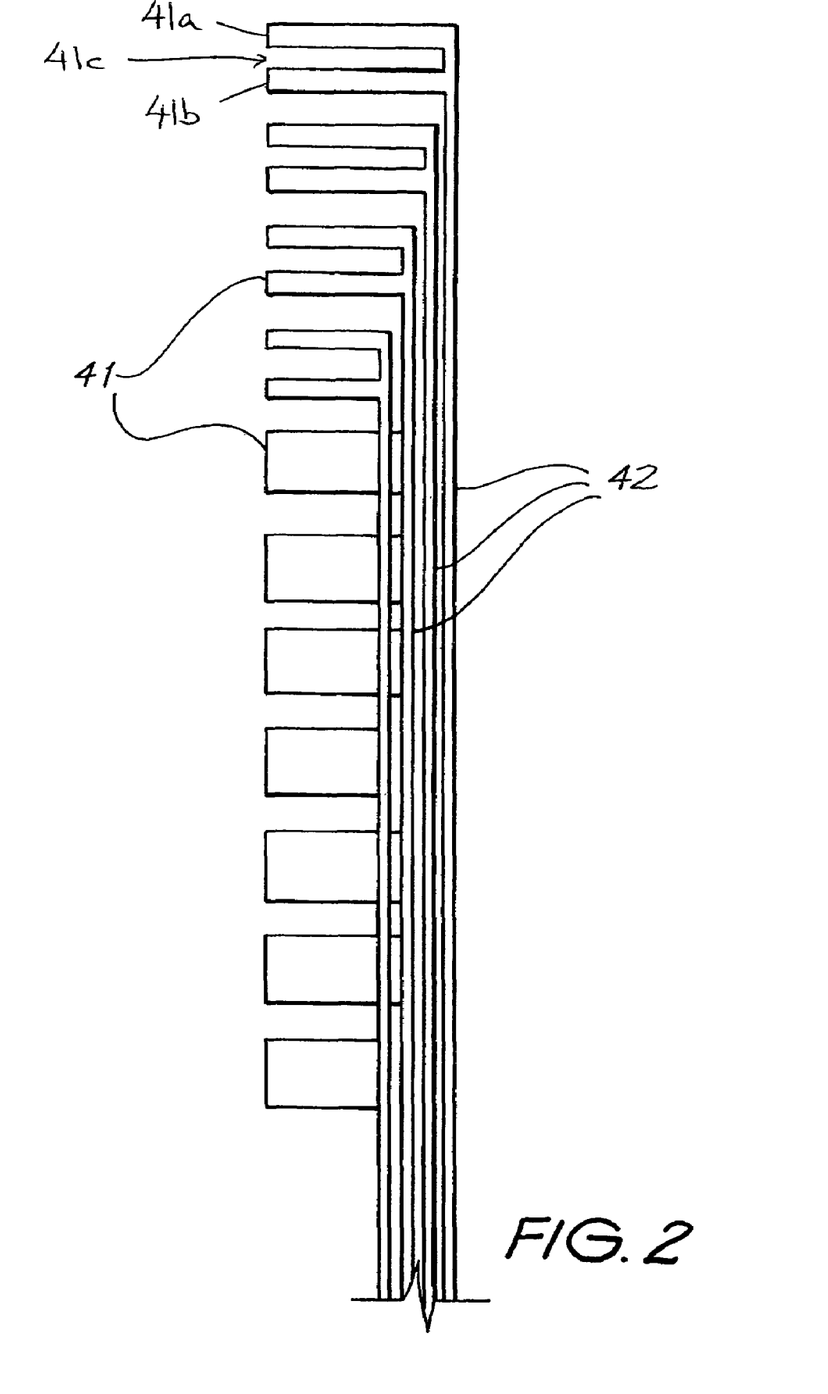
FIG. 2 is a plan view of stacked sets of electrodes of an electrode array suitable for use in a cochlear implant system according to the present invention.

While the sets of electrodes are stacked one upon the other, it will be appreciated that the actual position of the electrodes 41 from the respective sets are not necessarily vertically aligned. Rather, the set immediately above its lower set may be laterally offset so as to ensure the electrodes are visible from beneath the stack. A drawing depicting a part of an example of a longitudinal array of electrodes 41 according to the present invention is depicted in FIG. 2.

Figure 1A:
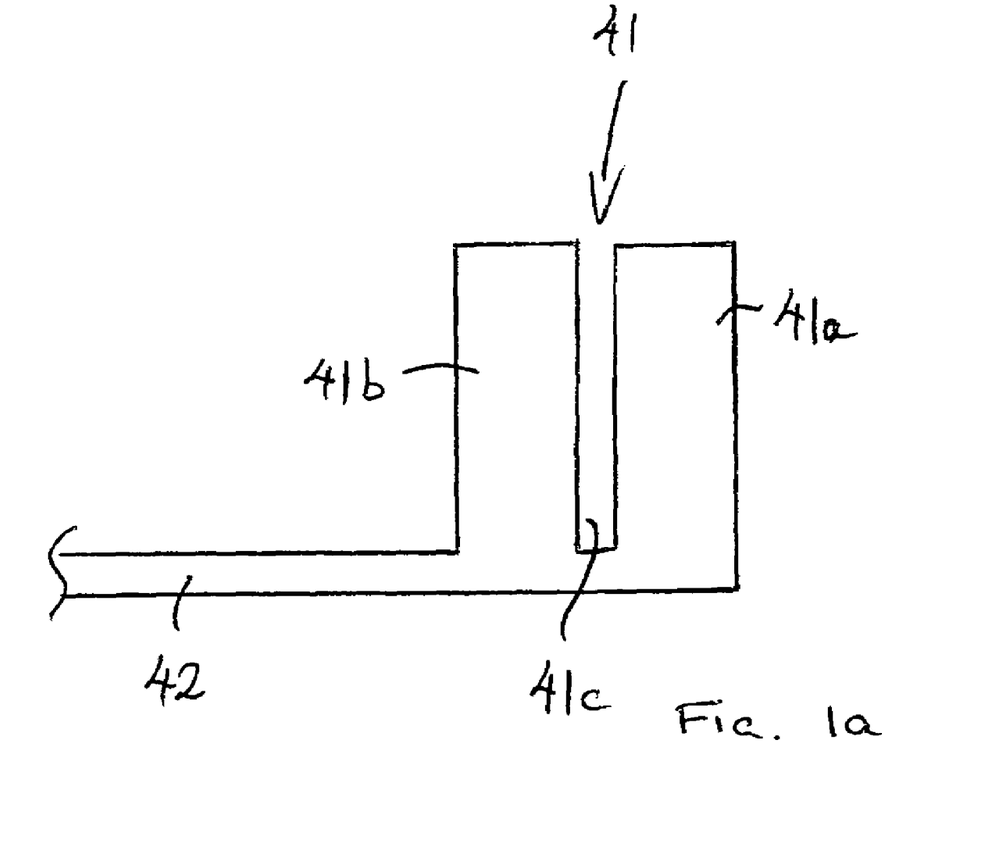
FIGS. 1a and 1b are enlarged plan views and FIG. 1c is an enlarged perspective view of adjustable electrodes for use in the array depicted in FIG. 1.

As is depicted more clearly in FIG. 1a, each of the electrodes 41 of electrode set 55 can be so-called split electrodes. Each electrode in this set is comprised of a first portion 41a and a second portion 41b, with the portions being separated by a longitudinal gap 41c. On manufacture, the portions 41a, 41b extend outwardly in a plane from a common conducting portion or wire 42.

Figure 1B:
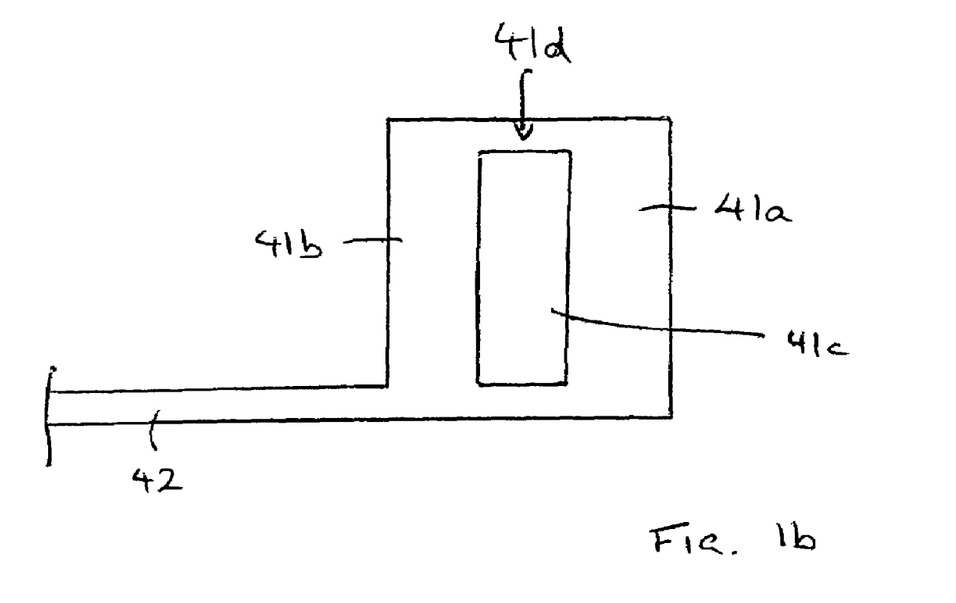

In another embodiment depicted in FIG. 1b, the gap 41c can be bridged by a bridge member 41d. As depicted, the bridge member 41d can extend between the portions 41a and 41b at a location distal the common conducting portion 42. While a single bridge member is depicted in FIG. 1b, more than one such bridge member could be present.

Figure 1C:
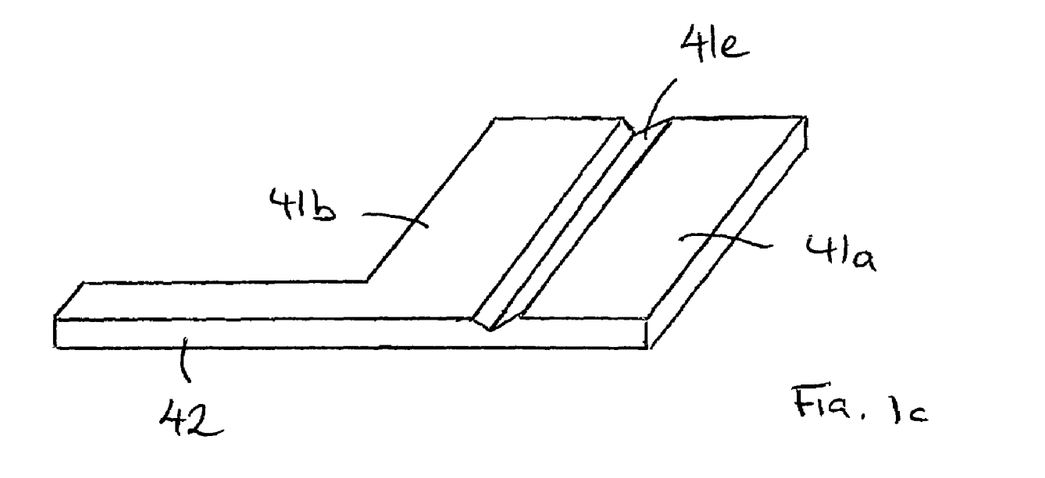

In another embodiment depicted in FIG. 1c, the portions can be linked by a region 41e that closes the gap between the portions 41a and 41b and which has a thickness less than that of the adjacent portions. As depicted, the region 41e can have a substantially V-shaped cross-section, with the electrode preferentially bendable at this location. It will be appreciated that the region 41e could only bridge a portion of the gap, for example, the region 41e could bridge the gap adjacent or near the common conducting wire 42.

Each electrode 41 has an associated wire 42 that extends from its respective electrode at least towards the trailing end of the carrier member in which the electrode array is supported. As depicted in FIG. 1, each wire extends lineally away from its electrode in a parallel arrangement with adjacent wires.

While the depicted embodiments depict the electrodes and "wires" as being formed from the same sheet of platinum as that used to form the electrodes, it will be appreciated that both the electrodes and wires could be formed using conventional processes, such as those described in the Applicant's U.S. Pat. No. 6,421,569, the contents of which is incorporated herein by reference, and still fall within the scope of the present invention. In this regard, each of the electrodes can be a conductive pad, made from a suitable biocompatible material, such as platinum, with conventional wires welded to each of the electrodes providing electrical conduction between each electrode to a location distal the electrode array. For example, FIG. 3 could be readily interpreted as depicting conductive platinum pads 41 to which conventional wires are welded and which then extend back through the length of the carrier member 60.

Once the stack is formed, the hitherto at least substantially planar electrodes 41 are preferably deformed so as to at least partially extend in a third dimension. In a preferred embodiment, each of the electrodes is curved out of the plane of the wires 42 for each set of electrodes. The curvature can be substantially semi-circular. A mandrel can be used to form the curvature in the electrodes.

Once the electrodes 41 have been deformed to have a substantially semi-circular curvature, each of the electrodes 41 are further folded about a longitudinal axis of the array 40. This folding of the electrodes 41 serves to bend the electrodes around the wires 42 of the array. The electrodes are preferably folded together and define a lumen that extends through the array 40. An example of the curvature of individual electrodes is depicted in FIG. 3.

Once the electrode array 40 is complete it is encapsulated in a further layer of a biocompatible relatively insulating material such as silicone to form an electrode carrier member 60. Silastic MDX 4-4210 is an example of one suitable silicone for use in the formation of the carrier member 60.

The step of forming the carrier member 60 can comprise mounting the array in a mould and filling the mould with the silicone and allowing it to cure. In this arrangement, the electrodes are positioned in the mould so as to not be coated with the silicone. In the arrangement depicted in FIG. 3, the carrier member is moulded in a spirally-curved configuration and preferentially adopts this configuration unless straightened by the presence of a stylet or other straightening device. In FIG. 3, the degree of curvature of the depicted carrier member is to be taken as illustrative only.

Figure 3:
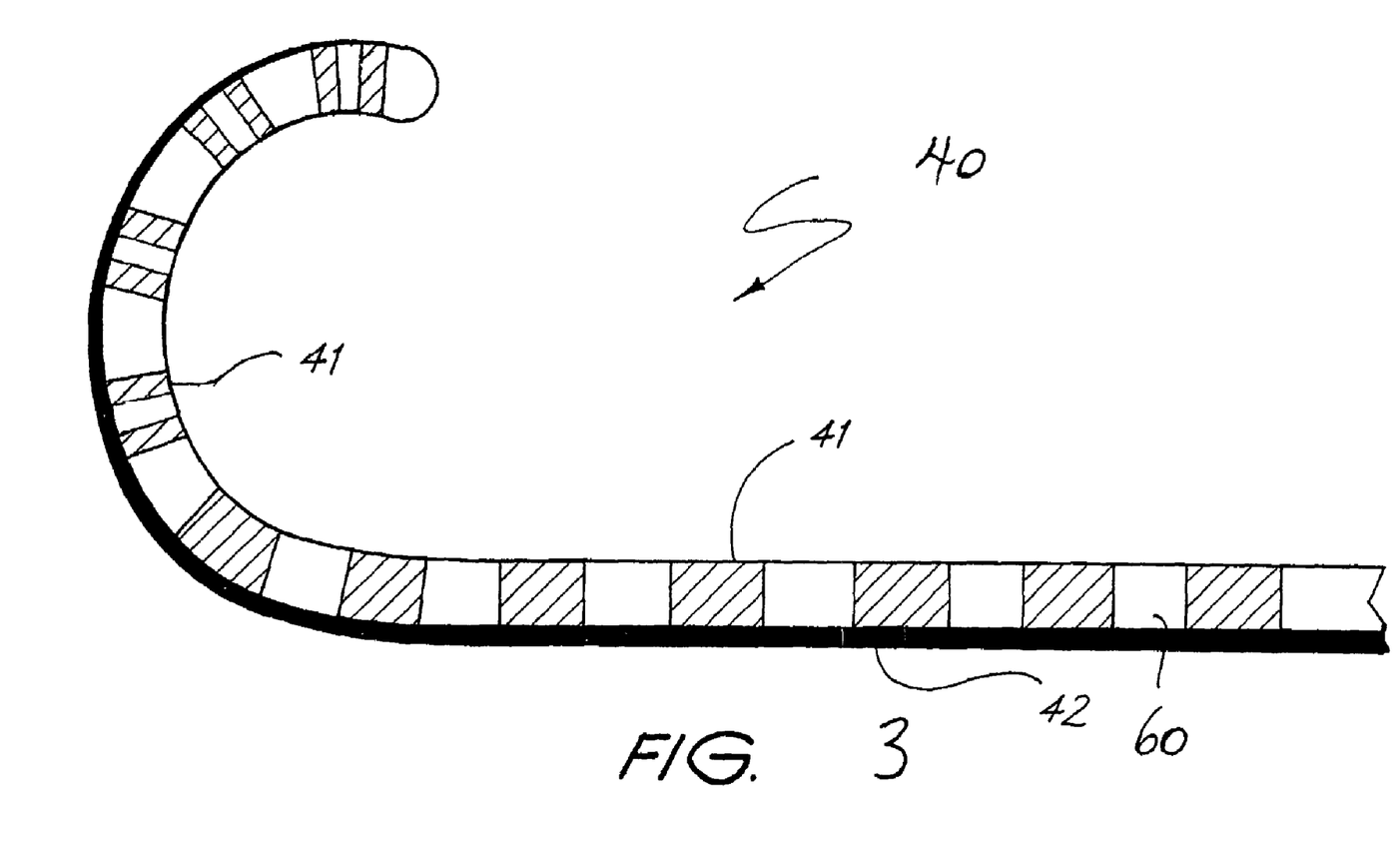
FIG. 3 is a view of a carrier member with a stylet at least partially retracted thereby allowing the carrier member to adopt a more pronounced curvature.

In FIG. 3, the stylet passes through a lumen in the carrier member 60 formed by the folding of the electrodes 41 as defined above. When the carrier member 60 is in the configuration depicted in FIG. 3, the stylet has been at least partially retracted to allow the carrier member 60 to begin to adopt its preferred spirally curved configuration.

As the carrier member begins to curve, the adjustable nature of the electrodes 41 adjacent the tip of the carrier 60 allows these electrodes to adjust in orientation relative to each other and so allows the array to adopt a tighter curvature than would otherwise by the case. Such an arrangement ensures that the stimulating surface area of the electrode elements throughout the array can be kept relatively constant, thereby ensuring a uniform current spread from each of the electrodes employed in the array, from the most basal electrode to the most apical electrode. This arrangement therefore overcomes the need to reduce the surface area/size of the most apical electrodes to enable that region to be at its most flexible to achieve a greater amount of curvature.

While the depicted embodiment has adjustable electrodes adjacent the tip of the carrier, the array could be constructed of adjustable electrodes and non-adjustable electrodes, with the adjustable electrodes formed in the array at locations where that adjustability is a greater requirement. For example, each of 30 electrodes, or at least 20 electrodes that will be typically positioned past the basal turn, can be adjustable.

Further, whilst the depicted embodiment has electrodes arranged with a substantially semi-circular arc, the electrodes could be arranged in a more conventional substantially flat manner, such as that described in the Applicant's U.S. Pat. No. 6,421,569. In this regard, the adjustable electrodes still function to impart greater adjustability and/or flexibility in the appropriate regions of the array. Further, whilst the depicted embodiment has the electrodes and wires constructed from the one piece, it is also envisaged that the electrodes and the wires could be separately constructed and welded into connection in a more conventional manner.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A cochlear implant comprising:
   a flexible elongate carrier member comprising at least one stimulating split electrode, said split electrode comprising:
      a first electrode portion;
      a second electrode portion adjacent to and spaced from said first electrode portion so as to define a gap therebetween, wherein said first electrode portion and said second electrode portion are adjustable in orientation relative to each other; and
      a common conducting portion directly electrically connecting said first electrode portion to said second electrode portion regardless of relative orientation of said first and second portions.

2. The implant of claim 1, wherein said split electrode further comprises:
   at least one flexible bridge member extending though said gap, connected to said first and second electrode portions, and wherein said bridge member is configured to limit changes in said relative orientation of said first and second portions.

3. The implant of claim 2,
   wherein said at least one flexible bridge member and said first and second electrode portions have substantially the same thickness.

4. The implant of claim 2, wherein said first and second electrode portions are elongate having substantially parallel longitudinal axes, and wherein said gap is an elongate gap having a longitudinal axis substantially parallel to said longitudinal axes of said electrode portions, and wherein said common conducting portion and said bridge member are longitudinally spaced in said gap.

5. The implant of claim 4, wherein said gap comprises proximal and distal ends and wherein said common conducting portion is positioned proximate to said proximal end of said gap and wherein said bridge member is positioned proximate said distal end of said gap.

6. The implant of claim 1, wherein said split electrode further comprises:
   a linking member, extending through said gap and connected to said first and second electrode portions, configured to substantially fill said gap.

7. The implant of claim 6, wherein said linking member has a thickness that is less than a thickness of said first and second electrode portions.

8. The implant of claim 6,
   wherein said first and second electrode portions are elongate having substantially parallel longitudinal axes, and wherein said gap is an elongate gap having a longitudinal axis substantially parallel to said longitudinal axes of said first and second portions, and
   wherein said linking member comprises an approximately linear groove extending substantially parallel to said longitudinal axis of said gap, said groove configured to allow said split electrode to bend at said groove.

9. The implant of claim 6, wherein said linking member, common conducting portion, first electrode portion and second electrode portion comprise regions of a unitary split electrode.

10. The implant of claim 1,
    wherein said first and second electrode portions are rectangular and longitudinally extend from said common conducting portion, and wherein said gap is a rectangular elongate gap positioned between said first and second rectangular electrode portions.

11. An electrode assembly comprising:
    a flexible elongate carrier member comprising at least one stimulating split electrode, said split electrode comprising:
       a first electrode portion;
       a second electrode portion adjacent to and spaced from said first electrode portion so as to define a gap therebetween, wherein said first electrode portion and said second electrode portion are adjustable in orientation relative to each other; and
       a common conducting portion disposed in said gap directly electrically connecting said first electrode portion to said second electrode portion while allowing specified changes in relative orientation between said first and second portions.

12. The assembly of claim 11, wherein said split electrode further comprises:
    at least one flexible bridge member extending though said gap, connected to said first and second electrode portions, and wherein said bridge member is configured to limit changes in relative orientation of said first and second portions to said specified changes in relative orientation of said first and second portions.

13. The assembly of claim 12, wherein said at least one flexible bridge member has a thickness substantially equal to that of said first and second electrode portions.

14. The assembly of claim 12, wherein said first and second electrode portions are elongate having substantially parallel longitudinal axes, and wherein said gap is an elongate gap having a longitudinal axis substantially parallel to said longitudinal axes of said first and second electrode portions, and wherein said common conducting portion and said bridge member are longitudinally spaced in said elongate gap.

15. The assembly of claim 11, wherein said split electrode further comprises:
    a linking member extending through said gap, connected to said first and second electrode portions, wherein said linking member is configured to substantially fill said gap.

16. The assembly of claim 15, wherein said linking member has a thickness less than a thickness of said electrode portions.

17. The assembly of claim 15,
    wherein said linking member, common conducting portion, first electrode portion and second electrode portion comprise regions of a unitary split electrode.

18. The assembly of claim 11,
    wherein said first and second electrode portions are rectangular and longitudinally extend from said common conducting portion, and wherein said gap is a rectangular elongate gap having a longitudinal axis substantially parallel to longitudinal axes of said first and second electrode portions;

wherein said linking member includes a substantially linear groove extending substantially parallel to said longitudinal axis of said gap configured to allow said split electrode to bend at said groove.

19. The assembly of claim 11, further comprising:
a plurality of electrodes comprising:
said at least one split electrode; and
two or more electrodes having a single electrode portion,
wherein said at least one split electrode is interspersed between said two or more electrodes having a single portion.

20. An electrode array for a tissue-stimulating prosthesis, comprising:
a plurality of stimulating electrodes, wherein at least one of said electrodes comprises:
a common conducting portion; and
at least two electrically connected electrode portions extending outwardly from said common conducting portion, wherein said at least two electrically connected portions are adjustable in orientation relative to each other; and
a region configured to link said electrode portions that hilly or substantially fills any gap between said electrically connected portions, and which has a thickness less than that of said electrically connected portions.

21. The array of claim 20, wherein said region that fully or substantially fills any gap between said portions has a substantially V-shaped cross-section configured to allow said electrode to bend at said cross section.

22. An electrode array for a tissue-stimulating prosthesis, comprising:
a plurality of stimulating electrodes, wherein at least one of said electrodes comprises:
a common conducting portion;
at least two electrically connected portions extending outwardly from said common conducting portion to define a gap therebetween, and adjustable in orientation relative to each other; and
one or more bridge members extending through said gap, connected to said electrode portions at a location distal said common conducting portion.

23. The array of claim 22, wherein said one or more bridge members have a thickness equal to that of said electrode portions.

24. An electrode assembly for a tissue-stimulating prosthesis, comprising:
at least one stimulating split electrode comprising:
a first electrode region;
a second electrode region adjacent to and spaced from said first electrode region, wherein said first electrode region and said second electrode region are adjustable in orientation relative to each other;
an elongate intermediate region positioned between said first and second electrode regions configured to separate said electrode regions; and
a common conducting region directly electrically connecting said first electrode region to said second electrode region regardless of relative orientation of said first and second electrode regions.

25. The electrode assembly of claim 24, wherein said intermediate region comprises a gap, and wherein at least one flexible bridge connected to said first and second electrode regions extends through said gap.

26. The electrode assembly of claim 25, wherein said at least one flexible bridge member and said first and second electrode regions have substantially the same thickness.

27. The electrode assembly of claim 25, wherein said first and second electrode regions have substantially parallel longitudinal axes, and wherein said gap is an elongate gap having a longitudinal axis substantially parallel to said longitudinal axes of said electrode regions, and wherein said common conducting region and said bridge member are longitudinally spaced in said gap.

28. The electrode assembly of claim 24, wherein said intermediate region comprises:
a linking region connected to said first and second electrode regions, said linking region configured to permit said split electrode to bend at said linking region 29. The electrode assembly of claim 28, wherein said linking region has a substantially V-shaped cross-section.

30. The electrode assembly of claim 28, wherein said first and second electrode regions have substantially parallel axes, and wherein said linking region has a longitudinal axis substantially parallel to said longitudinal axes of said first and second regions, and
wherein said linking region includes an approximately linear groove extending substantially parallel to said axis of said linking region configured to allow said adjustable electrode to bend at said groove 31. The electrode assembly of claim 28, wherein said linking region has a length that is substantially the same as the lengths of said first and second electrode regions.

* * * * *